(12) United States Patent
Murata et al.

(10) Patent No.: US 9,349,963 B2
(45) Date of Patent: May 24, 2016

(54) PHOTOELECTRIC CONVERSION ELEMENT AND SOLID-STATE IMAGING APPARATUS

(75) Inventors: Masaki Murata, Tokyo (JP); Ayumi Nihei, Tokyo (JP)

(73) Assignee: SONY CORPORATION, Tokyo (JP)

( * ) Notice: Subject to any disclaimer, the term of this patent is extended or adjusted under 35 U.S.C. 154(b) by 57 days.

(21) Appl. No.: 13/583,882

(22) PCT Filed: Mar. 14, 2011

(86) PCT No.: PCT/JP2011/001463
§ 371 (c)(1),
(2), (4) Date: Sep. 10, 2012

(87) PCT Pub. No.: WO2011/118148
PCT Pub. Date: Sep. 29, 2011

(65) Prior Publication Data
US 2013/0026341 A1    Jan. 31, 2013

(30) Foreign Application Priority Data

Mar. 23, 2010  (JP) ................. 2010-066441

(51) Int. Cl.
| | |
|---|---|
| *C12Q 1/68* | (2006.01) |
| *H01L 51/00* | (2006.01) |
| *C09K 9/02* | (2006.01) |
| *C07C 211/54* | (2006.01) |
| *H01L 31/00* | (2006.01) |
| *B32B 27/32* | (2006.01) |
| *H01L 51/40* | (2006.01) |
| *C07D 311/02* | (2006.01) |
| *H01L 27/30* | (2006.01) |

(52) U.S. Cl.
CPC .......... *H01L 51/0061* (2013.01); *C07C 211/54* (2013.01); *C09K 9/02* (2013.01); *H01L 27/307* (2013.01); *Y02E 10/549* (2013.01); *Y02P 70/521* (2015.11)

(58) Field of Classification Search
USPC ............... 250/200, 206; 428/220; 438/22, 99; 549/283, 320; 136/263; 257/40
See application file for complete search history.

(56) References Cited

U.S. PATENT DOCUMENTS

| | | |
|---|---|---|
| 2006/0011084 A1 | 1/2006 | Perkins |
| 2006/0110840 A1* | 5/2006 | Araki .............................. 438/22 |

(Continued)

FOREIGN PATENT DOCUMENTS

| | | |
|---|---|---|
| JP | 2006-054448 | 2/2006 |
| JP | 2006-339424 | 12/2006 |
| JP | 2007-088033 | 4/2007 |

(Continued)

OTHER PUBLICATIONS

Sakamoto et al., "Visible-Light Phtochromism of Triarylamine- or Ferrocene-Bound Diethynylethenes that Switches Electronic Communication between Redox Sites and Luminescence", Chem Eur J, 2008, 14, 6978-6986.

(Continued)

*Primary Examiner* — Bijan Ahvazi
(74) *Attorney, Agent, or Firm* — Hazuki International, LLC (57) ABSTRACT

A photoelectric conversion material is provided and includes an organic material having an absorbing coefficient of about $1.5 \times 10^5$ (cm$^{-1}$) or more and that is represented by the following formula (1). In the formula (1), each of $R_1$ to $R_{20}$, and each of $X_1$ to $X_8$ is one of a hydrogen atom and a substituent.

6 Claims, 6 Drawing Sheets

(56) References Cited

U.S. PATENT DOCUMENTS

2009/0223566 A1 9/2009 Mitsui et al.
2011/0077416 A1* 3/2011 Nishihara et al. ............ 549/283

FOREIGN PATENT DOCUMENTS

| JP | 2007-123707 | 5/2007 |
| JP | 2007-311647 | 11/2007 |
| JP | 2011-057564 | 3/2011 |

OTHER PUBLICATIONS

Kollenz et al, "New Isoindigoide Dyes from Heterocyclic 2,3-Diones—Synthesis and Thermal Rearrangement", Tetrahedron, vol. 52, No. 15, 5427-5440, 1996.

Tocco et al, "Evaluation of Photoluminescence Properties of Some Poly(ethylene glycol)—Supported Coumarin Derivatives", Molecules 2009, 14, 1044-1055.

Extended European Search Report dated Aug. 1, 2013 in corresponding European Patent Application No. 11758960.6.

Creation of novel molecular families of bridged, Mikihiro Hayashi, et al., Jun. 28, 2011.

Synthesis and photochemical property of new diethynylethene derivatives with triarylamine moieties, Mikihiro Hayashi, et al., The Chemical Society of Japan, 3PB-067, Jun. 28, 2011.

Japanese Office Action issued Sep. 24, 2013 in corresponding Japanese Patent Application No. 2010-066441.

Japanese Article 2 PA 66.

Chinese Office Action issued Jul. 28, 2014 in corresponding Chinese Application No. 201180014041.0.

Singapore Search Report issued Jun. 20, 2014 in corresponding Singapore Application No. 201206693-2.

* cited by examiner

PHOTOELECTRIC CONVERSION ELEMENT AND SOLID-STATE IMAGING APPARATUS

CROSS REFERENCES TO RELATED APPLICATIONS

The present application is a national stage of International Application No. PCT/JP2011/001463 filed on Mar. 14, 2011 and claims priority to Japanese Patent Application No. 2010-066441 filed on Mar. 23, 2010, the disclosure of which is incorporated herein by reference.

BACKGROUND

The present disclosure relates to a photoelectric conversion element and a solid-state imaging apparatus.

Photoelectric conversion elements using an organic material (organic photodiodes) can photoelectrically convert only a specific color (wavelength zone). Due to this characteristic, when the photoelectric conversion elements are used as photoelectric conversion elements in a solid-state imaging apparatus, a structure in which sub-pixels are laminated can be obtained, which structure cannot be obtained from a known solid-state imaging apparatus constituted of sub-pixels, which are made of a combination of on-chip-color-filters (OCCF) and photoelectric conversion elements, in a two-dimensional array. The photoelectric conversion elements, accordingly, can receive incident light with high efficiency, and therefore a solid-state imaging apparatus using them can be expected to have higher sensitivity. In addition, the photoelectric conversion elements have an advantage in which false colors are not generated because of a lack of necessity of demosaic processing.

On the other hand, structures of organic photoelectric conversion elements used in solid-state imaging apparatuses are the same as or similar to those of various organic thin film photovoltaic cells (see, for example, Japanese Patent Application Laid-open No. 2006-339424, Japanese Patent Application Laid-open No. 2007-123707, Japanese Patent Application Laid-open No. 2007-311647, and Japanese Patent Application Laid-open No. 2007-088033), and improvement of photoelectric conversion efficiencies is aimed for.

In general, organic materials have higher resistance, and very lower mobility and carrier density than silicon semiconductor materials. Photoelectric conversion elements using the organic material, therefore, have not reached to show the characteristics of sensitivity and responsiveness comparable to those of photoelectric conversion elements using inorganic materials as typified by known silicon semiconductor materials.

CITATION LIST

Patent Literature

PTL 1: Japanese Patent Application Laid-open No. 2006-339424

PTL 2: Japanese Patent Application Laid-open No. 2007-123707

PTL 3: Japanese Patent Application Laid-open No. 2007-311647

PTL 4: Japanese Patent Application Laid-open No. 2007-088033

Non Patent Literature

NPL 1: "Synthesis and photochemical property of new diethynylethene derivatives with triarylamine moieties", The Chemical Society of Japan, the 89th Spring Council (2009), 3PB-067

SUMMARY

Organic materials having a higher absorbing coefficient than silicon semiconductor materials are known (see, for example, "Synthesis and photochemical property of new diethynylethene derivatives with triarylamine moieties", The Chemical Society of Japan, the $89^{th}$ Spring Council (2009), 3PB-067). The article, however, states only that the new diethynylethene derivatives and cyclized derivatives synthesized therefrom are used as light-emitting materials, and it is silent about the photoelectric conversion element.

The present embodiments have been made under the circumstances described above, and it is desirable to provide photoelectric conversion elements using organic materials having high selective light-absorbing properties and a high photoelectric conversion efficiency, and solid-state imaging apparatuses including such photoelectric conversion elements.

In an embodiment, photoelectric conversion material includes an organic material having an absorbing coefficient of about $1.5 \times 10^5$ $(cm^{-1})$ or more and that is represented by the following formula (1).

In the formula (1), each of $R_1$ to $R_{20}$, and each of $X_1$ to $X_8$ is one of a hydrogen atom and a substituent selected from the group consisting of an alkyl group, a cycloalkyl group, an alkenyl group, an alkynyl group, an aryl group, an arylalkyl group, a heteroaromatic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, a hydroxy group, a mercapto group, a silyl group, a nitroso group, a nitro group, a carboxylic acid cyanide group, an isocyanide group, a thiocyanate group, an isothiocyanate group, an aldehyde group, a thioaldehyde group, a keto group, a thioketo group, and a hydrazide group.

In an embodiment, the photoelectric conversion material has an absorbing coefficient of about $1.53 \times 10^5$ $(cm^{-1})$ or more.

In an embodiment, the organic material is represented by the following formula (2).

(2)

In an embodiment, the organic material is represented by the following formula (3).

(3)

In an embodiment, the organic material is a triarylamine dye.

In another embodiment, a photoelectric conversion element includes a photoelectric conversion material layer including an organic material represented by the following formula (1).

(1)

In the formula (1), each of $R_1$ to $R_{20}$, and each of $X_1$ to $X_8$ is one of a hydrogen atom and a substituent selected from the group consisting of an alkyl group, a cycloalkyl group, an alkenyl group, an alkynyl group, an aryl group, an arylalkyl group, a heteroaromatic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, a hydroxy group, a mercapto group, a silyl group, a nitroso group, a nitro group, a carboxylic acid cyanide group, an isocyanide group, a thiocyanate group, an isothiocyanate group, an aldehyde group, a thioaldehyde group, a keto group, a thioketo group, and a hydrazide group.

In an embodiment, the organic material has an absorbing coefficient of about $1.5 \times 10^5$ ($cm^{-1}$) or more.

In an embodiment, the organic material has an absorbing coefficient of about $1.53 \times 10^5$ ($cm^{-1}$) or more.

In an embodiment, the organic material has an absorbing coefficient alpha (T) ($cm^{-1}$), and a film thickness of the photoelectric conversion material layer (nm) satisfies the following relationship:

$$\alpha(T) \geq 2.3 \times 10^7 / T$$

In an embodiment, the organic material has a molar absorbing coefficient epsilon of about $1 \times 10^4$ ($dm^3 \cdot mol^{-1} \cdot cm^{-1}$) or more.

In an embodiment, the organic material has a molar absorbing coefficient epsilon of about $3 \times 10^4$ ($dm^3 \cdot mol^{-1} \cdot cm^{-1}$).

In an embodiment, the organic material is represented by the following formula (2).

(2)

In an embodiment, the organic material is represented by the following formula (3).

(3)

In an embodiment, the organic material is a triarylamine dye.

In an embodiment, a light absorption spectrum of the photoelectric conversion material layer has a light absorption peak at a wavelength of about 550 plus or minus 20 nm.

In an embodiment, a light absorption spectrum of the photoelectric conversion material layer has a local maximal value in a wavelength range of about 400-700 nm.

In an embodiment, a thickness of the photoelectric conversion material layer ranges from about $1\times10^{-8}$ m to about $5\times10^{-7}$ m.

In an embodiment, a thickness of the photoelectric conversion material layer ranges from about $1\times10^{-7}$ m to about $1.8\times10^{-7}$ m.

In an embodiment, the photoelectric conversion element further comprises a substrate, and a plurality of the photoelectric conversion material layers are formed on the substrate.

In another embodiment, a method of operating a photoelectric conversion element includes irradiating a photoelectric conversion material layer, and producing a current. In this embodiment, the photoelectric conversion material layer includes an organic material represented by the following formula (1).

(1)

In the formula (1), each of $R_1$ to $R_{20}$, and each of $X_1$ to $X_8$ is one of a hydrogen atom and a substituent selected from the group consisting of an alkyl group, a cycloalkyl group, an alkenyl group, an alkynyl group, an aryl group, an arylalkyl group, a heteroaromatic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, a hydroxy group, a mercapto group, a silyl group, a nitroso group, a nitro group, a carboxylic acid cyanide group, an isocyanide group, a thiocyanate group, an isothiocyanate group, an aldehyde group, a thioaldehyde group, a keto group, a thioketo group, and a hydrazide group.

In an embodiment, the organic material has an absorbing coefficient of about $1.5\times10^5$ $(cm^{-1})$ or more.

In an embodiment, the organic material has an absorbing coefficient of about $1.53\times10^5$ $(cm^{-1})$ or more.

In an embodiment, the organic material is represented by the following formula (2).

(2)

In an embodiment, the organic material is represented by the following formula (3).

(3)

In an embodiment, the organic material is a triarylamine dye.

In an embodiment, a light absorption spectrum of the photoelectric conversion material layer has a light absorption peak at a wavelength of about 550 plus or minus 20 nm.

In an embodiment, a light absorption spectrum of the photoelectric conversion material layer has a local maximal value in a wavelength range of about 400-700 nm.

In an embodiment, the photoelectric conversion material layer has a thickness ranging from about $1 \times 10^{-8}$ m to about $5 \times 10^{-7}$ m.

In an embodiment, the photoelectric conversion material layer has a thickness ranging from about $1 \times 10^{-7}$ m to about $1.8 \times 10^{-7}$ m.

In another embodiment, a method of performing photoelectric conversion includes irradiating a photoelectric conversion material to produce an electrical response. In this embodiment, the photoelectric conversion material includes an organic material represented by the following formula (1).

(1)

In the formula (1), each of $R_1$ to $R_{20}$, and each of $X_1$ to $X_8$ is one of a hydrogen atom and a substituent selected from the group consisting of an alkyl group, a cycloalkyl group, an alkenyl group, an alkynyl group, an aryl group, an arylalkyl group, a heteroaromatic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, a hydroxy group, a mercapto group, a silyl group, a nitroso group, a nitro group, a carboxylic acid cyanide group, an isocyanide group, a thiocyanate group, an isothiocyanate group, an aldehyde group, a thioaldehyde group, a keto group, a thioketo group, and a hydrazide group.

In another embodiment, a photoelectric conversion apparatus includes a photoelectric conversion material layer including an organic material represented by the following formula (1).

(1)

carbonyl group, an aryloxycarbonyl group, a sulfamoyl group, an acyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, a hydroxy group, a mercapto group, a silyl group, a nitroso group, a nitro group, a carboxylic acid cyanide group, an isocyanide group, a thiocyanate group, an isothiocyanate group, an aldehyde group, a thioaldehyde group, a keto group, a thioketo group, and a hydrazide group.

In another embodiment, a solid state imaging apparatus includes an imaging area including at least one photoelectric conversion element including a photoelectric conversion material layer, the photoelectric conversion material layer including an organic material represented by the following formula (1).

(1)

In the formula (1), each of $R_1$ to $R_{20}$, and each of $X_1$ to $X_8$ is one of a hydrogen atom and a substituent selected from the group consisting of an alkyl group, a cycloalkyl group, an alkenyl group, an alkynyl group, an aryl group, an arylalkyl group, a heteroaromatic ring, a heterocyclic group, an alkoxy group, a cycloalkoxy group, an aryloxy group, an alkylthio group, a cycloalkylthio group, an arylthio group, an alkoxy- In the formula (1), each of $R_1$ to $R_{20}$, and each of $X_1$ to $X_8$ is one of a hydrogen atom and a substituent selected from the group consisting of an alkyl group, a cycloalkyl group, an alkenyl group, an alkynyl group, an aryl group, an arylalkyl group, a heteroaromatic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, a hydroxy group, a mercapto group, a silyl group, a nitroso group, a nitro group, a carboxylic acid cyanide group, an isocyanide group, a thiocyanate group, an isothiocyanate group, an aldehyde group, a thioaldehyde group, a keto group, a thioketo group, and a hydrazide group.

In the photoelectric conversion elements according to the embodiments, or the photoelectric conversion elements forming the solid-state imaging apparatus, the photoelectric conversion material layer is formed from the material having the structural formula (1), the structural formula (2), or the structural formula (3), which is generally called triarylamine dye, and the organic material having such a structural formula has a high absorbing coefficient (alpha). For this reason, the photoelectric conversion material layer using it can be thinner, and the defects of the previous organic materials such as high resistance, low mobility, and low carrier density can be overcome. Thus, a photoelectric conversion element or a solid-state imaging apparatus having high sensitivity and high-speed responsiveness can be provided. The electric intensity E applied to the photoelectric conversion material layer can be made larger when an identical electrical potential is applied, by making the thickness of the photoelectric conversion material layer thinner. Therefore, even if the mobility or the carrier density is low, a high photocurrent can be obtained. Moreover, a degree of freedom of a molecular design is high, and thus various derivatives can be designed. Because the photoelectric conversion material layer absorbs light with a specific wavelength, an on-chip-color-filter is not necessary, and the forming of the photoelectric conversion element into a multi-layer structure can be attempted.

Additional features and advantages are described herein, and will be apparent from the following Detailed Description and the figures.

DETAILED DESCRIPTION

Hereinafter, embodiments will be explained based on Examples below with reference to the drawings. However, the present embodiments are not limited to Examples, and various numerical values and materials in Examples are merely typical examples. The explanations will be made in the following order.

1. General explanations of the photoelectric conversion elements and the solid-state imaging apparatuses according to the first to third embodiments.

2. Example 1 (photoelectric conversion elements and solid-state imaging apparatuses according to the first to third embodiments), and others.

(General explanations of the photoelectric conversion elements and the solid-state imaging apparatuses according to the first to third embodiments)

In the photoelectric conversion elements according to the first to third embodiments or the photoelectric conversion elements forming the solid-state imaging apparatuses according to the first to third embodiments (hereinafter which may be collectively referred to as the "photoelectric conversion elements of the present embodiment"), an electrode on the light entering side is desirably formed from a transparent conductive material. The electrode is referred to as the "transparent electrode." The transparent conductive material forming the transparent electrode may include indium-tin oxide (including ITO, Sn-doped $In_2O_3$, crystalline ITO and amorphous ITO), IFO (F-doped $In_2O_3$), tin oxide ($SnO_2$), ATO (Sb-doped $SnO_2$), FTO (F-doped $SnO_2$), zinc oxide (including Al-doped ZnO, B-doped ZnO, and Ga-doped ZnO), indium oxide-zinc oxide (IZO), titanium oxide ($TiO_2$), spinel oxides, and oxides having a $YbFe_2O_4$ structure. The transparent electrodes formed from such a material usually have a high work function and function as an anode electrode. A method of forming the transparent electrode depends on the material forming the transparent electrode, and may include physical vapor deposition methods (PVD methods) such as vacuum deposition methods, reactive vapor deposition methods, various sputtering methods, electron-beam vapor deposition method, and ion plating methods, various chemical vapor deposition methods (CVD methods) including pyrosol methods, organic metal compound-pyrolyzing methods, spraying method, dipping method, and MOCVD method, and electroless and electrolytic plating methods. In some cases, the other electrode may be also formed from the transparent conductive material.

The conductive material constituting the first or second electrode, which is used when transparency is not required, is preferably a conductive material having a high work function (for example, phi=4.5 eV to 5.5 eV), if the first electrode or second electrode is used as the anode electrode (positive electrode), i.e., as an electrode for withdrawing positive holes, and may specifically include gold (Au), silver (Ag), chromium (Cr), nickel (Ni), palladium (Pd), platinum (Pt), iron (Fe), iridium (Ir), germanium (Ge), osmium (Os), rhenium (Re), and tellurium (Te). On the other hand, when the first or second electrode is used as the cathode electrode (negative electrode), i.e., as an electrode for withdrawing electrons, it is preferable to form the electrode from a conductive material having a low work function (for example, phi=3.5 eV to 4.5 eV), and may specifically include alkali metals (such as Li, Na, and K) and fluorides or oxides thereof; alkaline earth metals (such as Mg and Ca) and the fluorides or oxides thereof; aluminum (Al), zinc (Zn), tin (Sn), thallium (Tl), sodium-potassium alloy, aluminum-lithium alloy, magnesium-silver alloy, rare earth metals such as indium and ytterbium, and alloys thereof. Or, the material for forming the first electrode or the second electrode may include metals such as platinum (Pt), gold (Au), palladium (Pd), chromium (Cr), nickel (Ni), aluminum (Al), silver (Ag), tantalum (Ta), tungsten (W), copper (Cu), titanium (Ti), indium (In), tin (Sn), iron (Fe), cobalt (Co), and molybdenum (Mo), or alloys containing those metal elements, conductive particles of those metal, conductive particles of the alloy containing the metal, polysilicon containing an impurity, conductive substances such as carbon materials, oxide semiconductors, carbon nanotubes, and graphene. The electrode may have a laminated structure having the layers containing those elements. In addition, the material forming the first electrode and the second electrode may also include organic materials (conductive polymers) such as poly(3,4-ethylenedioxythiophene)/polystyrene sulfonic acid [PEDOT/PSS]. The conductive material may be mixed with a binder (polymer) to give a paste or ink, which is cured, and thus obtained electrode may be used.

The method of forming the first or second electrode depends on the material forming it, and may include various PVD methods described below; various CVD methods including MOCVD method; various coating methods described below; lift-off methods; sol-gel methods; electrodeposition methods; shadow mask methods; plating methods such as electrolytic plating methods, electroless plating methods, or the combination thereof; and spraying methods and combinations, if necessary, with patterning technology.

In the photoelectric conversion elements of the embodiments described above, it is possible to make a wavelength (lambda$_{max}$) of a light absorption peak 550 plus or minus 20 nm in the light absorption spectrum of the photoelectric conversion material layer. A half-bandwidth of the light absorption peak is desirably 120 nm or less. That is, when a wavelength corresponding this half-bandwidth is indicated as lambda$_{1/2}$ and lambda$_{1/2}$ (provided that lambda$_{1/2}$> lambda$_{1/2}$), it is desirable to satisfy the formula:

$$\lambda_{1/2} - \lambda_{-1/2} \leq 130 \text{ (nm)}.$$

Furthermore, it is more desirable to satisfy the formulae:

$$\lambda_{1/2} \leq 610 \text{ (nm)} \text{ and}$$

$$\lambda_{-1/2} \geq 480 \text{ (nm)}$$

Or, in the photoelectric conversion elements of the embodiments and structures described above, it is possible to make the light absorption spectrum of the photoelectric conversion material layer so as to have one local maximal value in a wavelength range of 400 nm to 700 nm. Furthermore, in the photoelectric conversion elements of the embodiments and structures described above, the photoelectric conversion material layer desirably has an absorbing coefficient alpha (cm$^{-1}$) of $1\times10^5$ or more, preferably $1.5\times10^5$ or more. Or, a molar absorbing coefficient epsilon (dm$^3$ (mol$^{-1}$(cm$^{-1}$) is preferably $1\times10^4$ dm$^3$dot mol$^{-1}$dot cm$^{-1}$ or more, desirably $3\times10^4$ dm$^3$ dot mol$^{-1}$dot cm$^{-1}$ or more.

The photoelectric conversion elements of the embodiments and structures described above can have a structure in which the first electrode made of the transparent conductive material is formed on a transparent substrate, the photoelectric conversion material layer is formed on the first electrode, and the second electrode is formed on the photoelectric conversion material layer. Or, it can have a structure in which the first electrode is formed on the substrate, the photoelectric conversion material layer is formed on the first electrode, and the second electrode made of the transparent conductive material is formed on the photoelectric conversion material layer. Herein, the first and second electrodes are separated from each other, for example as the second electrode is formed above the first electrode.

The method of forming the photoelectric conversion material layer may include coating methods, PVD methods, and various CVD methods including MOCVD methods. The coating methods may include specifically spin coating methods; immersion methods; casting methods; various printing methods such as screen printing, inkjet printing, offset printing and gravure printing; stamping methods; spraying methods; and other various coating methods such as air doctor coater methods, blade coater methods, rod coater methods, knife coater methods, squeeze coater methods, reverse roll coater methods, transfer roll coater methods, gravure coater methods, kiss coater methods, cast coater methods, spray coater methods, slit orifice coater methods, and calendaring-coater methods. Solvents used in the coating method may include apolar or low polar organic solvents such as toluene, chloroform, hexane, and ethanol. The PVD methods may include various vacuum deposition methods such as electron beam heating methods, resistance heating methods, and flash vapor deposition methods; plasma vapor deposition methods; various sputtering methods such as bipolar sputtering methods, direct current sputtering methods, direct current magnetron sputtering methods, high-frequency sputtering methods, magnetron sputtering methods, ion beam sputtering methods, and bias sputtering methods; and various ion plating methods such as DC (direct current) methods, RF methods, multi-cathode methods, activation reaction methods, electric field vapor deposition methods, high frequency ion plating methods, and reactive ion plating methods. Or when a photoelectric conversion elements integrated is used in the solid-state imaging apparatus formed therefrom, methods utilizing pattern formation based on a PLD method (a pulse laser deposition method) may be adopted.

The thickness of the photoelectric conversion material layer is not limited, and may be, for example, from $1\times10^{-8}$ m to $5\times10^{-7}$ m, preferably from $2.5\times10^{-8}$ m to $3\times10^{-7}$ m, more preferably from $2.5\times10^{-8}$ m to $2\times10^{-7}$ m, even more preferably from $1\times10^{-7}$ m to $1.8\times10^{-7}$ m.

As the substrate, organic polymers (flexible polymeric materials in the shape of plastic film, sheet, plate or the like) such as polymethyl methacrylate (polymethyl methacrylate, PMMA), polyvinylalcohol (PVA), polyvinylphenol (PVP), polyether sulfone (PES), polyimide, polycarbonate (PC), polyethylene terephthalate (PET), and polyethylene naphthalate (PEN), as well as mica. When the substrate formed from the polymer material having flexibility is used, it is possible, for example, to incorporate or integrate the electric device into or with an electric apparatus having a curved surface shape. Or, as the substrate, various glass substrates, various glass substrates whose surface is applied with an insulating film, quartz substrates, quartz substrates whose surface is applied with an insulating film, silicon substrates whose surface is applied with an insulating film, and metal substrates made of various alloys and various metals such as stainless steel may also be exemplified. The insulating film may include silicon oxide-based materials (for example, SiO$_x$ and spin-on-glass (SOG)); silicon nitride (SiN$_y$); silicon oxide nitride (SiON); aluminum oxide (Al$_2$O$_3$); metal oxides, and metal salts. Conductive substrates whose surface is applied with the insulating film (substrates made of a metal such as gold or aluminum, or substrates made of highly oriented graphite) may also be used. The surface of the substrate is desirably smooth, but may have a roughness that does not exert adverse effects on the properties of the photoelectric conversion material layer. The adhesion between the first or second electrode and the substrate may be improved by forming a film of a silanol derivative on the substrate surface through silane-coupling method; forming a thin film of a thiol derivative, carboxylic acid derivative, or phosphoric acid derivative through an SAM method; or forming a thin film of an insulating metal salt or metal complex through a CVD method. The term the "transparent substrate" refers to a substrate formed from a material which does not excessively absorb incident light into the photoelectric conversion material layer through the substrate.

In some cases, the electrodes or the photoelectric conversion material layer may be coated with a coating layer. The material forming the coating layer may include silicon oxide-based materials; silicon nitrides ($SiN_y$); inorganic insulating materials, for example, highly dielectric insulation films of a metal oxide such as aluminum oxide ($Al_2O_3$), polymethyl methacrylate (PMMA); polyvinylphenol (PVP); polyvinylalcohol (PVA); polyimide; polycarbonate (PC); polyethylene terephthalate (PET); polystyrene; silanol derivatives (silane-coupling agents) such as N-2 (aminoethyl)3-aminopropyltrimethoxysilane (AEAPTMS), 3-mercaptopropyltrimethoxysilane (MPTMS), and octadecyltrichlorosilane (OTS); and organic insulating materials (organic polymers) such as straight-chain hydrocarbons having a functional group capable of bonding the electrode at its one end such as octadecanethiol or dodecyl isocyanate. The combination thereof may also be used. The silicon oxide-based material may include silicon oxides ($SiO_x$), BPSG, PSG, BSG, AsSG, PbSG, silicon oxide nitride (SiON), SOG (spin-on glass), and materials having a low-dielectric constant (for example, polyarylether, cycloperfluorocarbon polymers and benzocyclobutene, cyclic fluoroplastics, polytetrafluoroethylene, arylether fluoride, polyimide fluoride, amorphous carbon, and organic SOG).

The solid-state imaging apparatus may be a front-surface irradiation-type apparatus or a rear-surface irradiation-type apparatus, and can also be a single-plate type color solid-state imaging apparatus. The solid-state imaging element, if necessary, may be provided with an on-chip microlens or a light sealing layer, and drive circuits or wiring for driving the photoelectric conversion element (solid-state imaging element). If necessary, a shutter may be provided for controlling the incident light into the photoelectric conversion element, or an optical cut filter may be provided depending on the object of the solid-state imaging apparatus. When the solid-state imaging element in the solid-state imaging apparatus according to an embodiment is formed as a single layer of the photoelectric conversion element of an embodiment, the arrangement of the photoelectric conversion element may include a Bayer arrangement, an interline arrangement, a G-stripe RB check arrangement, a G-stripe RB complete check arrangement, a check complementary color arrangement, a stripe arrangement, an oblique stripe arrangement, a different-from-original-color arrangement, a field color difference sequential arrangement, a frame color difference sequential arrangement, an MOS arrangement, an improved MOS arrangement, a frame interleave arrangement, and a field interleave arrangement. Light sensors, image sensors, and photovoltaic cells can be formed from the photoelectric conversion elements of the embodiment, in addition to the imaging apparatuses (solid-state imaging apparatuses) such as television cameras.

EXAMPLE 1

Figure 1:
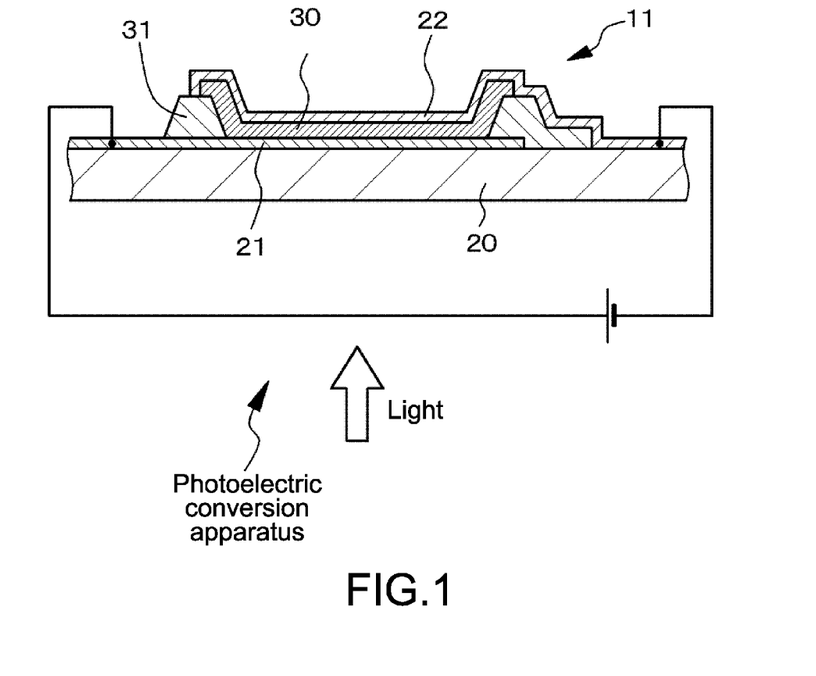
FIG. 1 is a schematic cross-sectional view of a photoelectric conversion element of Example 1.

Example 1 relates to the photoelectric conversion elements and the solid-state imaging apparatuses according to the first, second and third embodiments. FIG. 1 is a schematic cross-sectional view showing a photoelectric conversion element of Example 1. When the photoelectric conversion element of Example 1 is explained in line with the first, second, and third embodiments, the element includes: (a-1) a first electrode 21 and a second electrode 22 formed as separated; and (a-2) a photoelectric conversion material layer 30 formed between the first electrode 21 and the second electrode 22, in which the photoelectric conversion material layer 30 is formed from a material having the structural formula (1) described above, the structural formula (2) described above, or the structural formula (3) described above. A solid-state imaging apparatus of Example 1 includes the photoelectric conversion element of Example 1.

In the structural formula (1), $R_3$, $R_8$, $R_{13}$, and $R_{18}$ are "—O—$CH_3$"; $R_1$, $R_2$, $R_4$, $R_5$, $R_6$, $R_7$, $R_9$, $R_{10}$, $R_{11}$, $R_{12}$, $R_{14}$, $R_{15}$, $R_{16}$, $R_{17}$, $R_{19}$, and $R_{20}$ are hydrogen atoms; and $X_1$, $X_2$, $X_3$, $R_4$, $X_5$, $X_6$, $X_7$, and $X_8$ are hydrogen atoms. In the structural formula (2), $R_1$, $R_2$, $R_3$, and $R_4$ are "—O—$CH_3$".

In Example 1, the photoelectric conversion material layer 30 had an average thickness of 100 nm. The wavelength of the light absorption peak ($lambda_{max}$) in the light absorption spectrum of the photoelectric conversion material layer 30 is 550 plus or minus 20 nm, specifically 550 nm. Also, $lambda_{1/2}$=500 nm,
$lambda_{1/2}$=590 nm and the light absorption spectrum of the photoelectric conversion material layer 30 has one local maximal value within a wavelength range of 450 nm to 650 nm. Further, the photoelectric conversion material layer 30 has an absorbing coefficient alpha ($cm^{-1}$) of $1 \times 10^5$ or more, specifically $1.53 \times 10^5$ ($cm^{-1}$), and a molar absorbing coefficient epsilon ($dm^3 dot$ $mol^{-1} dot$ $cm^{-1}$) of $1 \times 10^4$ or more, specifically $5 \times 10^4$ $dm^3 dot$ $mol^{-1} dot$ $cm^{-1}$. The quinacridone, which has been used for years, has an absorbing coefficient alpha of $1.3 \times 10^5$ ($cm^{-1}$), and a molar absorbing coefficient epsilon ($dm^3 dot$ $mol^{-1} dot$ $cm^{-1}$) of $1.4 \times 10^4$ ($dm^3 dot$ $mol^{-1} dot$ $cm^{-1}$). As described above, the organic material forming the photoelectric conversion material layer 30 in Example 1 has the absorbing coefficient higher than that of the quinacridone, and therefore the increase in the photo current can be attained.

The first electrode 21, which is the one on the light entering side, is made of a transparent conductive material, specifically an indium-tin oxide (ITO) film having a thickness of 120 nm. The second electrode 22 is made of an aluminum (Al) film having a thickness of 100 nm. The first electrode 21 made of the transparent conductive material is formed on the transparent substrate 20, the photoelectric conversion material layer 30 is formed on the first electrode 21, and the second electrode 22 is formed on the photoelectric conversion material layer 30. As described above, the second electrode 22 is placed above the first electrode 21. Light enters into the photoelectric conversion material layer 30 through the substrate 20 and the first electrode 21. The substrate 20 is made of a quartz substrate having a thickness of 0.7 mm.

The photoelectric conversion element 11 in Example 1 can be produced by the following method. First, the first electrode 21 made of ITO having a thickness of 120 nm is formed on the substrate 20 in accordance with a lithographic technique using a photomask. Next, a protrusion 31 made of an insulating material is formed on the substrate 20 and the first electrode 21, and then the photoelectric conversion material layer 30 (a thickness: 100 nm) including a triarylamine dye shown by the structural formula (1), (2), or (3) is formed (formed as a film) over the first electrode 21 and the protrusion 31 in accordance with a vacuum deposition method using a metal mask. The substrate temperature was set to room temperature during the vacuum deposition, and the film making speed of the photoelectric conversion material layer 30 was set to 0.1 nm/second. Then, the second electrode 22 made of aluminum having a thickness of 100 nm is formed over the photoelectric conversion material layer 30 and the substrate 20 by a PVD method using a metal mask. The second electrode 22 was formed under conditions of a substrate temperature of 30 degrees Celsius and a film-making speed of the second electrode 22 of 0.5 nm/second. The protrusion 31 is formed so as to surround the area of the substrate 20 where the photoelectric conversion material layer 30 is to be formed. The first electrode 21 had a surface roughness of $R_a=0.3$ nm and $R_{max}=3.8$ nm. Prior to the film formation of the photoelectric conversion material layer 30, ultraviolet irradiation and ozone irradiation were performed on the backings, the first electrode 21 and the protrusion 31. It is generally desirable that the first electrode 21 have a surface roughness, $R_a$ of 0.3 nm or less.

Figure 2:
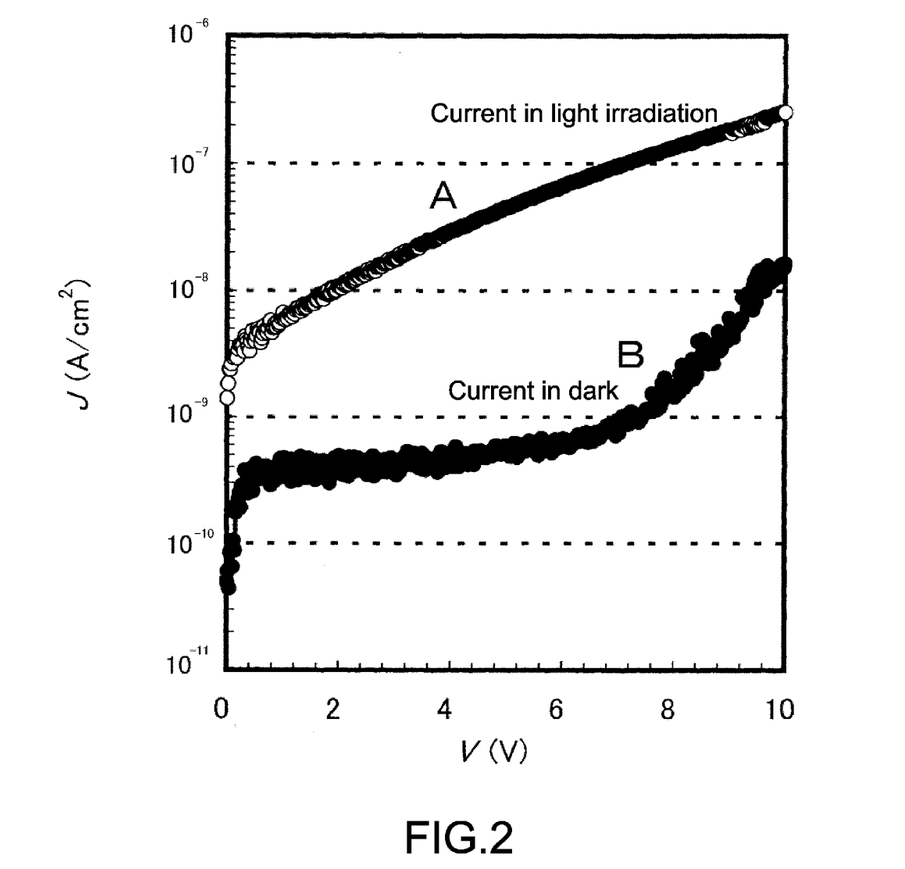
FIG. 2 is a graph showing a J-V characteristic obtained when light having a wavelength of 565 nm and at a certain light intensity (10 (W/cm$^2$) is applied to the photoelectric conversion element of Example 1.
Figure 3:
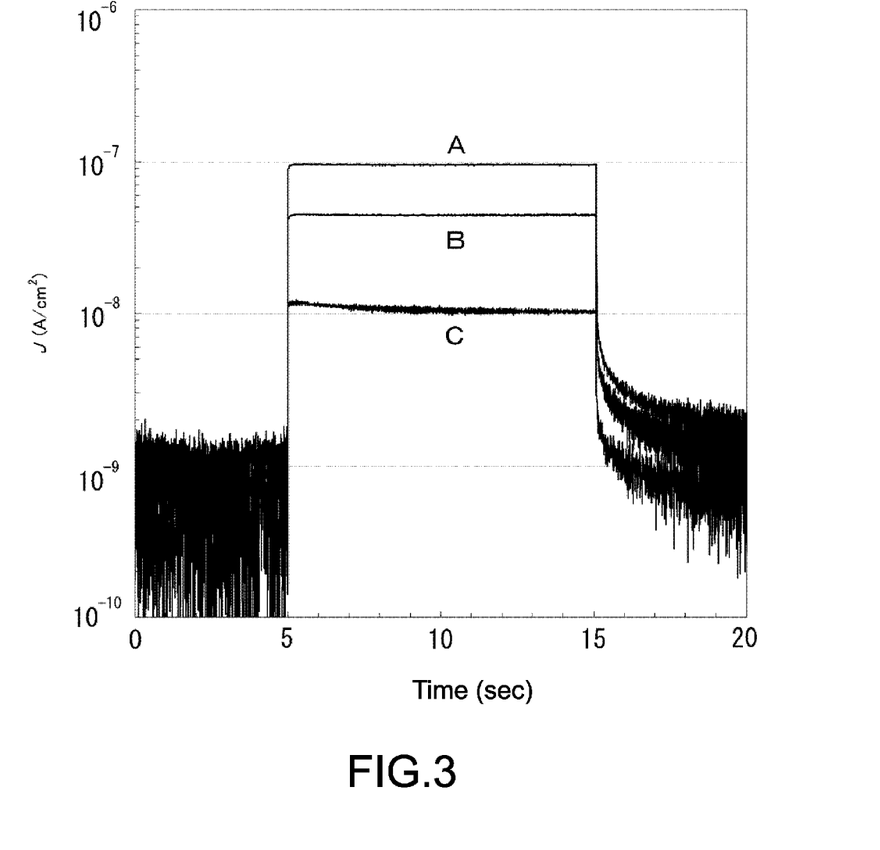
FIG. 3 is a graph showing a J-t characteristic obtained when light having a wavelength of 565 nm and at a certain light intensity (10 (W/cm$^2$) is applied to the photoelectric conversion element of Example 1.

Light having a wavelength of 565 nm and at a certain light intensity P (=10 micro W/cm$^2$) was applied to the photoelectric conversion material layer 30 of thus obtained photoelectric conversion element 11 of Example 1 through the transparent substrate 20 and the first electrode 21, and a predetermined voltage (a bias voltage) was applied to the first electrode 21, while the second electrode 22 was grounded. FIG. 2 shows a J-V characteristic obtained at that time, in which a curve "A" shows current values J (ampere/cm$^2$) obtained by the photoelectric conversion element 11. In FIG. 2, a curve "B" shows current values J (ampere/cm$^2$) in the dark, obtained when light is not applied. It is understood the current values J increase as the bias voltages are increased. FIG. 3 shows a J-t characteristic obtained when light having a wavelength of 565 nm and at a certain light intensity P (=10 micro W/cm$^2$) was applied. In FIG. 3, "A" shows data obtained when a voltage of 7 V was applied to the first electrode 21, "B" shows data obtained when a voltage of 5 V was applied to the first electrode 21, and "C" shows data obtained when a voltage of 2 V was applied to the first electrode 21, in the tests, light being applied from the fifth second to the fifteenth second.

Figure 4:
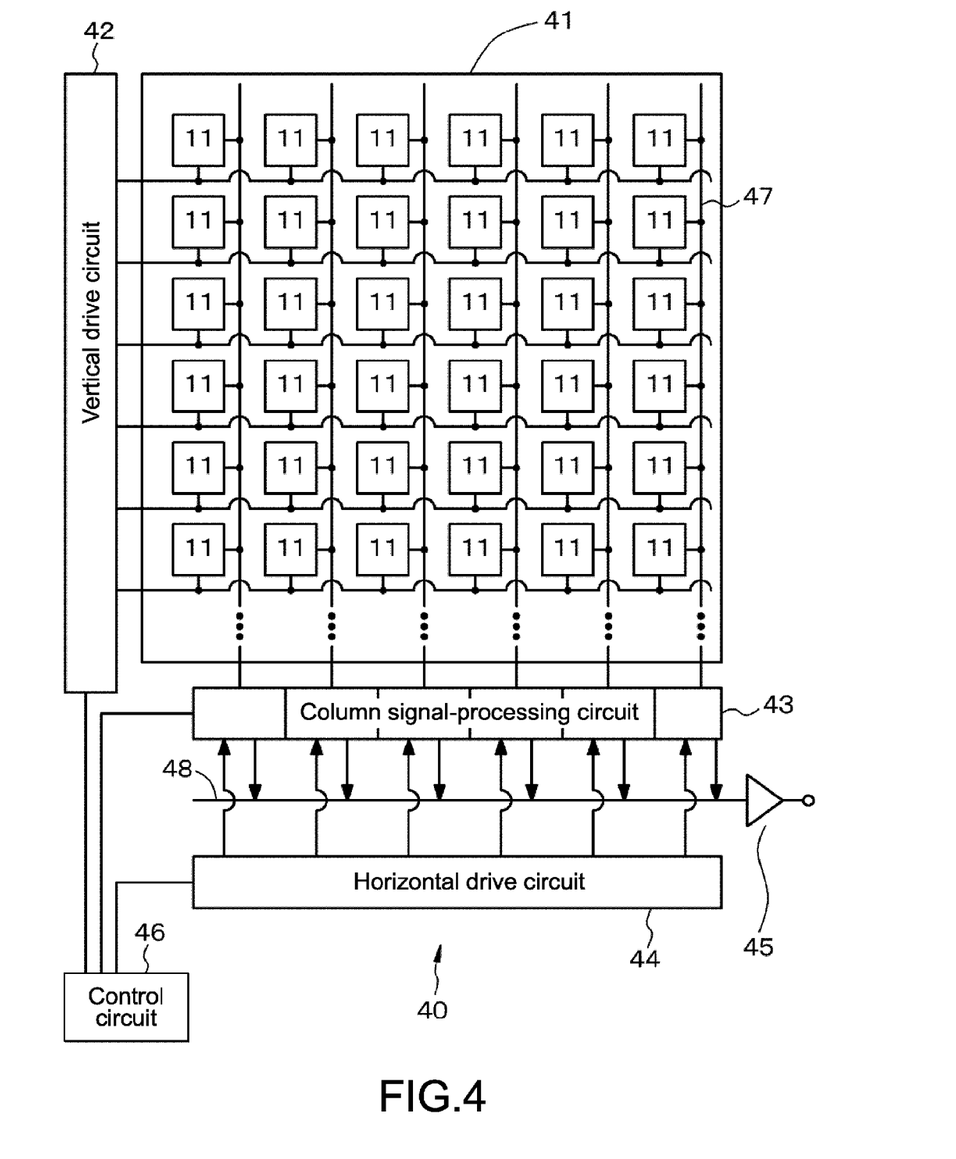
FIG. 4 is a conceptual diagram of a solid-state imaging apparatus of Example 1.

In FIG. 4, a conceptual diagram of the solid-state imaging apparatus (solid-state imaging element) of Example 1 is shown. The solid-state imaging apparatus 40 of Example 1 includes an imaging area 41 in which the photoelectric conversion elements 11, described above, are arranged in a two-dimensional array on a semiconductor substrate (for example, an Si substrate) and peripheral circuits such as a vertical drive circuit 42, a column signal-processing circuit 43, a horizontal drive circuit 44, an output circuit 45, a control circuit 46, and the like. These circuits may be formed with well known circuits or circuits with different circuit configurations (for example, various circuits used in common CCD and CMOS imaging apparatuses).

The control circuit 46 generates clock and control signals, which are the standards of the operation of the vertical drive circuit 42, the column signal-processing circuit 43, and the horizontal drive circuit 44, based on vertically synchronized signal, horizontally synchronized signal, and master clock. The generated clock and control signals are inputted into the vertical drive circuit 42, the column signal-processing circuit 43 and the horizontal drive circuit 44.

The vertical drive circuit 42 has, for example, a shift register, and sequentially and selectively scans each photoelectric conversion element 11 in the imaging area 41 in a vertical direction line by line. A pixel signal based on the current (signal) generated according to the intensity of light received in each of the photoelectric conversion elements 11 is sent to the column signal-processing circuit 43 via the vertical signal wire 47.

The column signal-processing circuits 43 are installed, for example, in every line of the photoelectric conversion elements 11, and subject the signals which are output from each line of the photoelectric conversion elements 11 to denoising and signal amplification in every photoelectric conversion element by signals from a black standard pixel (not shown in the Figure, formed in the area surrounding an effective pixel area). A horizontal selection switch (not shown in the Figure) is installed such that it is connected to the horizontal signal wire 48 in an output stage of the column signal-processing circuits 43.

The horizontal drive circuit 44 has, for example, a shift register, and sequentially selects each of the column signal-processing circuits 43 by sequentially outputting horizontal scanning pulses and outputs signals from each of the column signal-processing circuits 43 to the horizontal signal wire 48.

The output circuit 45 subjects signals, which are sequentially transmitted from each of the column signal-processing circuits 43 via the horizontal signal wire 48, to signal processing, and outputs them.

Figure 5A:
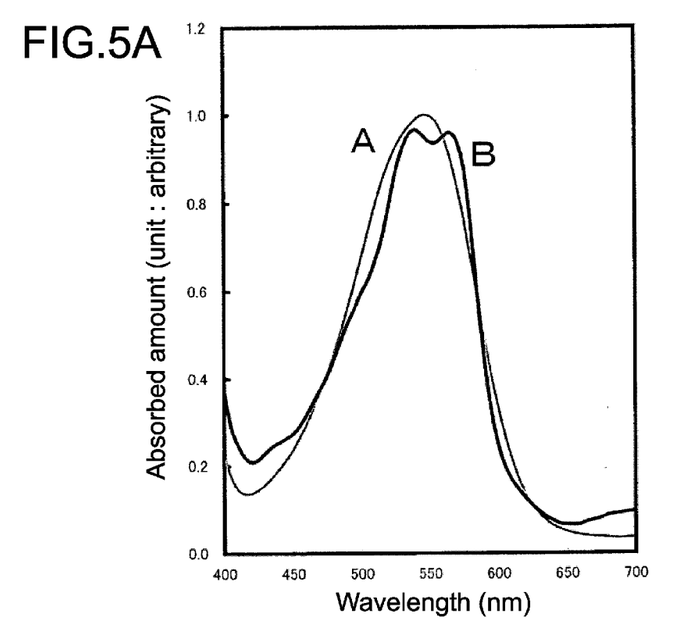
FIGS. 5A and 5B each show a light absorption spectrum of a triarylamine dye shown by the structural formula (3), a light absorption spectrum of a quinacridone, and a light absorption spectrum of a color filter.
Figure 5B:
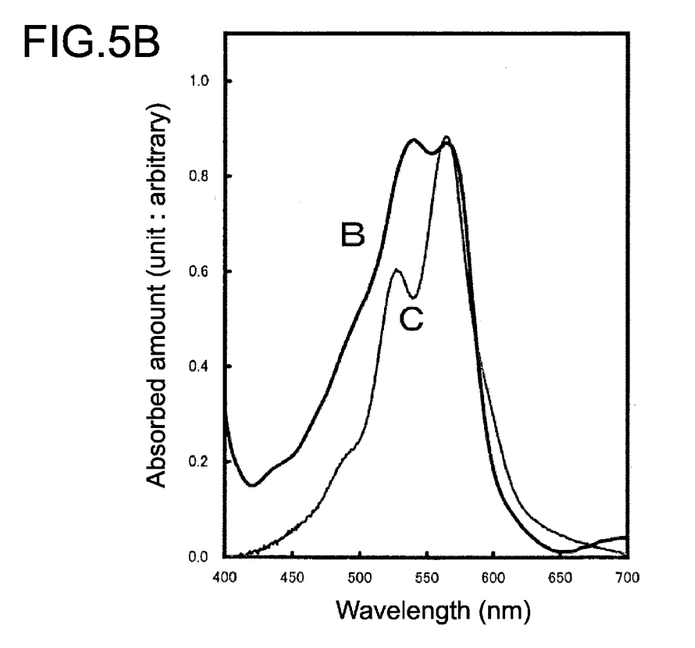

Here, because the photoelectric conversion material layer itself may function as a color filter, color separation can be performed even if no color filter is formed. FIG. 5A shows a light absorption spectrum of a triarylamine dye, shown by the structural formula (3) (shown as "A") and a light absorption spectrum of a magenta color filter adsorbing green (shown as "B"). FIG. 5B shows a light absorption spectrum of quinacridone (shown as "C") and the light absorption spectrum of the magenta color filter adsorbing green (shown as "B"). As described above, a wavelength of a light absorption peak (lambda$_{max}$) is 550 plus or minus 20 nm, specifically 550 nm, in a light absorption spectrum of the photoelectric conversion material layer 30, and the light absorption spectrum of the photoelectric conversion material layer 30 has one local maximal value within a wavelength range of 400 nm to 700 nm. From FIGS. 5A and 5B, it is understood that the triarylamine dye shown by the structural formula (3) has almost the same light-absorbing properties as the light absorption spectrum of the magenta color filter.

Figure 6:
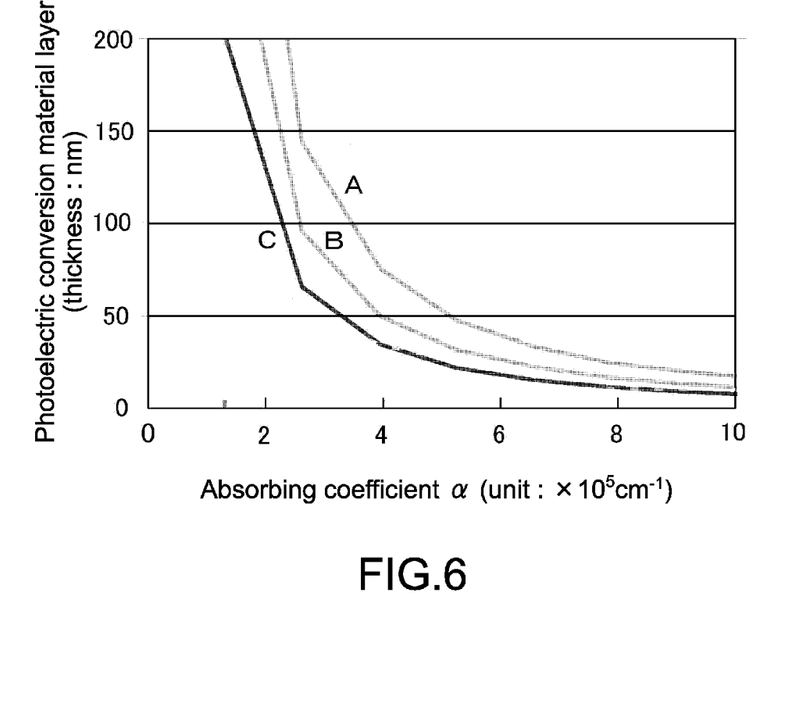
FIG. 6 is a graph showing the results of the relationship between an absorbing coefficient alpha and a photoelectric conversion material layer in various organic materials used in the photoelectric conversion element of Example 1.

Furthermore, the relationships between the absorbing coefficients alpha obtained from various organic materials and the photoelectric conversion material layer in the photoelectric conversion element of Example 1 are shown in FIG. 6. In FIG. 6, a curve "A" shows results obtained when a bias voltage is 1.35 V, a curve "B" shows results obtained when a bias voltage is 2.7 V, and a curve "C" shows results obtained when a bias voltage is 5.0 V. In FIG. 6, when a relationship between an absorbing coefficient alpha of a material forming the photoelectric conversion material layer and a thickness of the photoelectric conversion material layer is located at the upper right to the curves, an external photoelectric conversion efficiency increases. FIG. 6 indicates that when a material having an absorbing coefficient alpha of $1\times10^5$ cm$^{-1}$ is selected and a bias voltage is 5.0 V, it is necessary that the photoelectric conversion material layer has a film thickness of 200 nm or more, but when a material having an absorbing coefficient of $2\times10^5$ cm$^{-1}$ is selected, the same external conversion efficiency can be obtained even if the photoelectric conversion material layer has a film thickness of 140 nm. From these results, it can be understood that the higher the absorbing coefficient, the higher the external conversion efficiency even if the thickness of the photoelectric conversion material layer is made thinner. Specifically, it is desirable that the absorbing coefficient alpha (T) [unit: cm$^{-1}$] and the film thickness T of the photoelectric conversion material layer [unit: nm] satisfy the following relationship:

$$\alpha(T) \geq 2.3\times10^7/T$$

In the photoelectric conversion element of Example 1 or the photoelectric conversion element forming the solid-state imaging apparatus of Example 1, the photoelectric conversion material layer is made of the material shown by the structural formula (1), the structural formula (2), or the structural formula (3) and has a high absorbing coefficient. Therefore, the photoelectric conversion element or the solid-state imaging apparatus having high sensitivity and high-speed responsiveness can be provided. Also, the degree of freedom of the molecular design is high and various derivatives can be designed. Moreover, because the photoelectric conversion material layer absorbs light having a specific wavelength, an on-chip-color-filter is not necessary, and the photoelectric conversion element can be formed into a multi-layer structure.

When the photoelectric conversion element described in Example 1 is formed on, for example, a silicon semiconductor substrate, and one or more layers (for example two layers) of the photoelectric conversion areas are formed in the silicon semiconductor substrate which is located downward the photoelectric conversion element, a solid-state imaging apparatus having a structure in which the photoelectric conversion elements (light receiving areas) are laminated, or a structure in which sub-pixels are laminated, can be obtained. When such a solid-state imaging apparatus is used, for example, green light can be received by the photoelectric conversion element described in Example 1, and other colors can also be received by the one or more layers of the photoelectric conversion areas being formed in the silicon semiconductor substrate. In addition, the photoelectric conversion areas can be formed on a semiconductor substrate by an epitaxial growth method, instead of the formation of the photoelectric conversion areas in the silicon semiconductor substrate, or the photoelectric conversion areas can be formed on a silicon layer in a generally called SOI structure. When the photoelectric conversion element according to Examples of the present embodiments functions as a photovoltaic cell, light may be applied to the photoelectric conversion material layer while no voltage is applied between the first electrode and the second electrode.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A photoelectric conversion material comprising:
an organic material having an absorbing coefficient of about $1.5 \times 10^5$ (cm$^{-1}$) or more and that is represented by formula (1)

wherein, in the formula (1), one or more of $R_1$ to $R_{20}$, and one or more of $X_1$ to $X_8$ are hydrogen atoms and other of $R_1$ to $R_{20}$ and other of $X_1$ to $X_8$ are selected from the group consisting of an alkenyl group, an alkynyl group, an alkylthio group, a cycloalkylthio group, an arylthio group, and a sulfamoyl group.

2. The photoelectric conversion material according to claim 1, wherein the organic material has an absorbing coefficient of about $1.53 \times 10^5$ (cm$^{-1}$) or more.

3. The photoelectric conversion material according to claim 1, wherein the organic material is represented by formula (2)

wherein, in the formula (2), one or more of $R_3$, $R_8$, $R_{13}$ and $R_{18}$ and other of $R_3$, $R_8$, $R_{13}$ and $R_{18}$ are selected from the group consisting of the alkenyl group, the alkynyl group, the alkylthio group, the cycloalkylthio group, the arylthio group, and the sulfamoyl group.

4. The photoelectric conversion material according to claim 1, wherein the organic material is a triarylamine dye.

5. A photoelectric conversion material comprising:
an organic material having an absorbing coefficient of about $1.5 \times 10^5$ (cm$^{-1}$) or more and that is represented by formula (1)

(1)

wherein, in the formula (1), one or more of $R_1$ to $R_{20}$, and one or more of $X_1$ to $X_8$ are hydrogen atoms and other of $R_1$ to $R_{20}$ and other of $X_1$ to $X_8$ are further selected from the group consisting of an acyl group, an acyloxy group, an amide group, a carbamoyl group, a ureide group, a sulfinyl group, an alkylsulfonyl group, and a mercapto group.

6. A photoelectric conversion material comprising:
an organic material having an absorbing coefficient of about $1.5 \times 10^5$ (cm$^{-1}$) or more and that is represented by formula (1)

(1)

wherein, in the formula (1), one or more of $R_1$ to $R_{20}$, and one or more of $X_1$ to $X_8$ are hydrogen atoms and other of $R_1$ to $R_{20}$ and other of $X_1$ to $X_8$ are further selected from the group consisting of a nitroso group, an isocyanide group, a thiocyanate group, an isothiocyanate group, an aldehyde group, a thioaldehyde group, a keto group, a thioketo group, and a hydrazide group.

* * * * *